US00PP13992P39

(12) United States Plant Patent
Austin

(10) Patent No.: US PP13,992 P3
(45) Date of Patent: Jul. 22, 2003

(54) SHRUB ROSE PLANT NAMED 'AUSPEET'

(75) Inventor: David C. H. Austin, Wolverhampton (GB)

(73) Assignee: David Austin Roses Limited, Albrighton (GB)

( * ) Notice: Subject to any disclaimer, the term of this patent is extended or adjusted under 35 U.S.C. 154(b) by 0 days.

(21) Appl. No.: 10/032,197

(22) Filed: Dec. 20, 2001

(65) Prior Publication Data

US 2003/0121079 P1 Jun. 26, 2003

(51) Int. Cl.[7] ..... A01H 5/00

(52) U.S. Cl. ..... Plt./104

(58) Field of Search ..... Plt./104, 102, 134, Plt./145

*Primary Examiner*—Bruce R. Campell
*Assistant Examiner*—June Hwu
(74) *Attorney, Agent, or Firm*—Klarquist Sparkman LLP

(57) ABSTRACT

Shrub rose plant having attractive, bushy growth and very large, full rounded blooms, opening to a shallow cup; the color of the flower varying from an almost buff yellow to lemon yellow.

1 Drawing Sheet

GENUS AND SPECIES

*Rosa hybrida.*

VARIETY DENOMINATION

'AUSpeet'.

SUMMARY OF INVENTION

The present invention relates to a new and distinct variety of rose plant of the shrub class which was originated by me by crossing an unnamed seedling, (unpatented), with an unnamed seedling (unpatented).

BACKGROUND OF THE INVENTION

The primary objective of this breeding was to produce a new rose variety having a very free-flowering and healthy plant with flowers of the classic English rose shape with a good fragrance.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Very large, full rounded blooms, opening to a shallow cup;
2. Attractive, bushy growth; and
3. Color of flowers varies from an almost buff yellow to lemon yellow.

Asexual reproduction of this new variety by budding onto *Rosa dumetorum laxa* rootstock, as performed at Albrighton, England, shows that the foregoing and all other characteristics and distinctions come true to form and are established and transmitted through succeeding propagations.

COMPARISON WITH PARENTS

'AUSpeet' has yellow flowers compared to the pink/apricot flowers of its seed parent and 136 petals as compared to the 55 to 75 petaled flower of its pollen parent.

COMPARISON WITH SIMILAR VARIETY

The most similar rose variety, 'AUSbaker', (U.S. Plant patent application Ser. No. 09/705,463) has a large, arching growth habit as compared to 'AUSpeet's' upright branching habit and 'AUSbaker's' leaves are smaller and the leaflets less rounded than those of 'AUSpeet'.

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

The following is a detailed description of my new rose cultivar with color descriptions using terminology in accordance with The Royal Horticultural Society (London) colour chart, except where ordinary dictionary significance of color is indicated.

Parentage:
*Seed parent.*—Unnamed Seedling (Unpatened).
*Pollen parent.*—Unnamed Seedling (Unpatented).

FLOWER

Observations made from plants of six years of age grown in a garden environment at Albrighton, England, July, 1998.

Blooming habit: Recurrent.
Bud:
*Size.*—About 0.5–1 inch long when the petals start to unfurl.

*Form*.—The bud form is globular.

*Color*.—When sepals first divide, bud color is Yellow Group RHS 12C with some mottling of Red Group 45C on the outermost petals. When half blown, the upper sides of the petals are Yellow Group RHS 12C; and the lower sides of the petals are Yellow Group 8D.

*Sepals*.—Color: Yellow-Green Group 144A. Length: 0.8 inch. Width: 0.5 inch. Shape: Ovate. Surface texture: Smooth but edges are hairy. There are three lightly appendaged sepals. There are two unappendaged sepals with hairy edges.

*Receptacle*.—Color: Yellow-Green Group 144B. Shape: Funnel. Size: Medium, about 0.4–0.5 inch long×0.5 inch wide. Surface: Smooth.

*Peduncle*.—Length: Medium, averaging about 2.7 inches. Surface: Smooth. Color: Yellow-Green Group 144C with Red-Purple Group 59B tinge. Strength: Erect.

Bloom:

*Size*.—Medium. Average open size is 3 inches.

*Borne*.—Several together in pyramidal clusters of four blooms.

*Stems*.—Strength: Normal. Average length is About 24 inches.

*Form*.—When first open: Bloom is cupped. Permanence: Outer petal edges curl slightly.

*Petalage*.—Number of petals under normal conditions: 136.

*Color*.—The upper sides of the petals are Yellow Group 8C on the inner portion and Yellow Group 8D on the outer portion. The reverse sides of the petals are Yellow Group 8C. The base of each petal is Yellow Group 9A. The major color on the upper side is Yellow Group 8C.

*Variegations*.—None.

*Discoloration*.—The general tonality at the end of the first day: Yellow Group 8B. At the end of the third day: Yellow Group 8A. As the bloom ages color fades to Yellow Group 4B.

*Fragrance*.—Strong and fruity.

Petals:

*Texture*.—Smooth and satiny.

*Shape*.—Orbicular.

*Margin*.—Frilled.

*Size*.—Length: 3.5 cm. Width: 3 cm.

*Apex shape*.—Rounded.

*Base shape*.—Rounded.

*Form*.—Tips slightly recurved on outer petals, heavily quilled in the center.

*Arrangement*.—Quartered in center.

*Petaloids*.—Average number: 9. Size: 3 mm width×5 mm height. Color: Yellow Group RHS 8B. Shape: Elliptical.

*Persistence*.—Petals drop off cleanly before drying.

*Lastingness*.—On the plant: Fair (about 7 days). As a cut flower: Fair (about 7 days).

Reproductive parts:

*Stamens*.—Number: 55. Anthers: Length: 3/32 inch. Color: Yellow-Orange Group 15B. Arrangement: Mixed with petaloids. Filaments: Color: Yellow-Orange Group 14A. Pollen: Color: Yellow-Orange Group 14B.

*Pistils*.—Number: 70.

*Styles*.—Color: Yellow-Green Group 150A. Length: 0.5 inch. Stigmas: Color: Yellow Group 13B. Length: 1/32 inch.

*Hips*.—None produced.

Plant:

*Form*.—Shrub, English.

*Growth*.—Upright, branching.

*Mature plant*.—Height: 3.5 feet. Width: 3 feet.

*Rootstock*.—'Dr. Huey' rootstock recommended for U.S.

Foliage: Number of leaflets on normal mid-stem leaves: 5–7.

*Size*.—Medium (5–7 inches long×5–7 inches wide).

*Quantity*.—Normal.

*Color*.—New foliage: Upper side: Green Group 137B with Greyed-Red Group 180A tint around edge. Lower side: Yellow-Green Group 146B. Old foliage: Upper side: Green Group 139A. Lower side: Yellow-Green Group 146A.

Leaflets:

*Size*.—About 2.75 inches long×1.75 inches wide.

*Shape*.—Broadly oval.

*Tip shape*.—Acuminate.

*Base shape*.—Rounded.

*Texture*.—Leathery, semi-glossy.

*Edge*.—Serrated.

*Serrations*.—Single, medium.

*Petiole color*.—Green Group 138B.

*Petiole rachis*.—Color: Yellow-Green Group 145A. Underside: with prickles.

*Auricle shape, if present*.—Pointed.

*Stipules*.—Length: About 0.75 inch; Serrated.

*Disease resistance*.—Resistant to mildew, blackspot and rust under normal growing conditions.

*Pest resistance*.—Not tested.

Wood:

*New wood*.—Color: Yellow-Green Group 144B with Greyed-Purple Group 183C blush. Bark: Smooth.

*Old wood*.—Color: Yellow-Green Group 144A (slightly streaky) with Greyed-Red Group 178B blush. Bark: Smooth.

Prickles:

*Quantity*.—On main canes from base: Few. On laterals from main canes: Few.

*Form*.—Hooked downward. Length: 0.25 inch.

*Color when young*.—Greyed-Purple Group 187B.

*Color when mature*.—Greyed-Purple Group 187A.

Small prickles:

*Quantity*.—On main stalks: None. On laterals: None.

Climate hardiness: Not tested.

I claim:

1. A new and distinct variety of rose plant of the shrub class, substantially as herein shown and described, characterized particularly by its attractive, bushy growth and very large, full rounded blooms, opening to a shallow cup; the color of the flower varying from an almost buff yellow to lemon yellow.

* * * * *

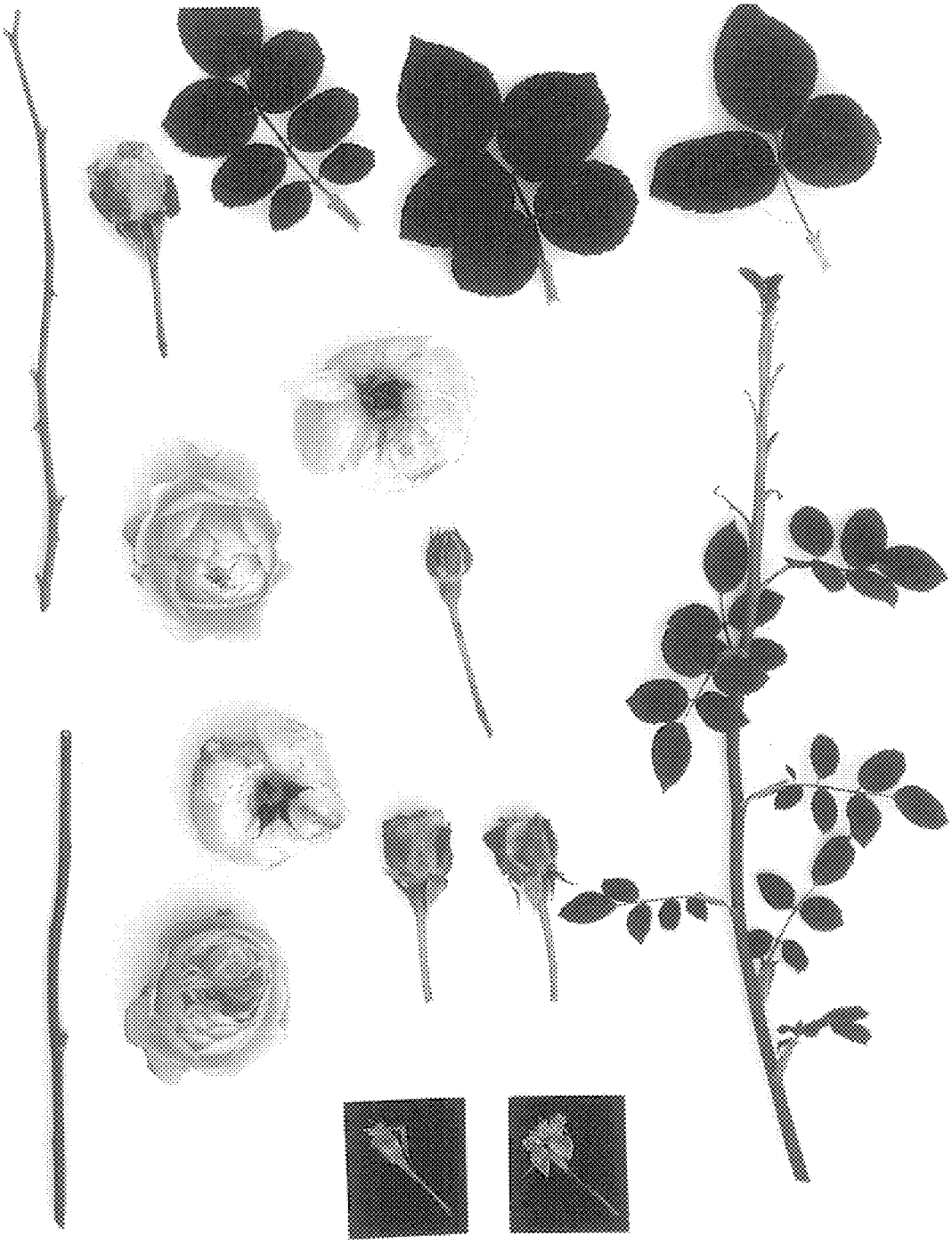
P/2/92 AUSPEET